United States Patent [19]

Guterman et al.

[11] Patent Number: 4,745,056
[45] Date of Patent: May 17, 1988

[54] STREPTOMYCES SECRETION VECTOR

[75] Inventors: Sonia Guterman, Belmont; Janice Pero, Lexington; Phillips Robbins, Arlington, all of Mass.

[73] Assignee: Biotechnica International, Inc., Cambridge, Mass.

[21] Appl. No.: 663,842

[22] Filed: Oct. 23, 1984

[51] Int. Cl.[4] .................. C12P 21/00; C12N 15/00; C12N 1/20; C12N 7/00
[52] U.S. Cl. .................................. 435/68; 435/172.3; 435/253; 435/320; 435/886; 435/896; 935/29; 935/48
[58] Field of Search .............. 435/172.3, 68, 6, 3, 435/7, 29, 253; 935/29, 48, 60, 75

[56] References Cited

U.S. PATENT DOCUMENTS 4,338,397 7/1982 Gilbert .................................. 435/68
4,513,086 4/1985 Fayerman et al. .................. 435/317

OTHER PUBLICATIONS

Palva, I. et al, "Secretion of E. coli β-Lactamase from B. subtilis . . . " Proc. Natl. Acad. Sci. USA, 79: 5582–5586, 1982.
Poole, K. et al, "Secretion of Alkaline Phosphatase . . . " FEMS Microbiol Letters, 16: 25–29, 1983.
Rottman, F. M. et al, "Cloning of Bovine Growth Hormone Gene . . . " Chemical Abstracts, 98: 102101z, 1983.
Thompson et al. (1980), Nature, 286: 525–527.
Thompson et al. (1983), PNAS (USA), 80: 5190–5194.
Burnett et al. (1984), Abstracts of the Annual Meeting of the American Society for Microbiology H98, p. 107.
Robbins et al. (1981), J. Biol. Chem. 256: 10640–10644.
Robbins et al. (1984), J. Biol. Chem. 259: 7577–7583.
Kendall et al. (1984), Gene 29: 315–321.
Katz et al. (1983), J. General Microbiol., 129: 2703–2714.
Palva (1983), Gene 22: 229–235.
Wright et al. (1983), J. Cell Biochem. Suppl. Part 7B, p. 346, #1408.

Primary Examiner—Thomas G. Wiseman
Assistant Examiner—Thomas D. Mays

[57] ABSTRACT

Cloning vectors are disclosed to obtain secretion of a desired protein from a host Streptomyces when a structural gene coding for the protein is inserted into the vector. The vector has: (1) regulatory DNA that includes a promoter sequence effective to start transcription in the host Streptomyces and DNA that encodes a ribosome-binding site; (2) a DNA sequence that codes for a signal sequence that occurs naturally in a Streptomyces strain or that derives from such a DNA sequence; and (3) at least one engineered restriction endonuclease recognition site positioned for the insertion of a structural gene, the DNA that encodes a signal sequence and attached structural gene being transcribed and translated together under the control of the regulatory DNA. Expression vectors are disclosed which include a structural gene coding for a desired protein so positioned. Streptomyces cells containing the vector and methods of using them to produce the desired protein are disclosed. Finally, an alkaline phosphatase gene is inserted in secretion vectors for use in a method of evaluating the ability of those vectors to cause secretion in host gram positive bacteria; the method may be used to evaluate either a potential host or a potential secretion vector.

26 Claims, 4 Drawing Sheets

STREPTOMYCES SECRETION VECTOR

BACKGROUND OF THE INVENTION

This invention relates to genetically engineered strains of bacteria of the genus Streptomyces. As used in this application, the term "Streptomyces bacteria" or "Streptomyces" means any bacterial strain that is a member of the genus Streptomyces as classified in Buchanan et al., *The Shorter Bergey's Manual For Determinative Bacteriology* (Williams & Wilkins 1982). The invention also relates to vectors for engineering Streptomyces and methods of producing desired compounds with the resulting engineered organisms.

For some time now, the pharmaceutical industry has used strains of Streptomyces to produce desired compounds, particularly antibiotics.

Vectors carrying various genes that are expressed in Streptomyces have been reported. Katz et al. (1983) J. General Microbiol. 129:2703-2714 report cloning a DNA fragment coding for tyrosinase from *S. antibioticus* DNA into two plasmids. The resulting hybrid plasmids are inserted in a strain of *S. lividans*. They report that most of the tyrosinase activity of *S. antibioticus* is secreted; in contrast, most of the activity remains intracellular in *S. lividans* clones. There is no indication of the mechanism for transport of the activity through the cell wall into the medium.

Thompson et al. (1980) Nature 286:525-527 report cloning the tsr gene from *S. azureus* which is expressed under its own promoter on various vectors.

Thompson et al. (1983) PNAS (USA) 80:5190-5194 report sequencing the *S. fradiae* aph (neomycin resistance) gene together with its promoter region. They also report that the aph gene has been incorporated into high copy-number, broad host-range vectors.

Burnett et al. (1984) Abstracts of the Annual Meeting of the American Society of Microbiology H98, p. 107, report cloning a 10-kb fragment from *S. lividans* containing a transcription start site and two structural genes (beta-galactosidase and Bgl protein). They have determined the sequence of that promoter region as well as of a ribosome-binding site.

Robbins et al. (1981) J. Biol. Chem. 256:10,640-10,644 report cloning the gene coding for the enzyme endo-N-acetylglucosaminidase (endo H) from *S. plicatus* into *E. coli* plasmid pBR322. The enzyme is expressed in *E. coli* and is found in the cytoplasmic, periplasmic, and supernatant fractions.

There have been reports of vectors that include a leader sequence which enables secretion of an expressed protein in other bacterial species. For example, see Gilbert U.S. Pat. Nos. 4,338,397 and 4,411,994 [*E. coli*]; and Palva et al. (1983) Gene 22:229-235 [*Bacillus subtilis*].

SUMMARY OF THE INVENTION

One aspect of the invention features, in general, a cloning vector engineered to receive a structural gene coding for a desired protein to cause expression of the gene in, and secretion of the protein from, a host Streptomyces bacterial strain. The vector comprises: (1) regulatory DNA which includes a promoter sequence effective to start transcription in the host Streptomyces and DNA that encodes a ribosome-binding site; (2) a DNA sequence that codes for a signal sequence, the DNA sequence deriving from DNA that occurs naturally in a Streptomyces strain and (3) at least one engineered restriction endonuclease recognition site positioned for the insertion of a structural gene, the DNA encoding a signal sequence and the inserted structural gene being transcribed and translated together under the control of the regulatory DNA. For convenience, we will use the term "protein" to include proteins or smaller peptides. By a sequence that "derives from" another sequence, we mean a sequence that is identical to that other sequence or is a naturally occurring or engineered variant or chemically synthesized copy or variant thereof that preserves the desired function. By a "signal sequence" we mean a portion of a protein that causes the protein or a fragment of it to be transported through a cell membrane.

In a second aspect, the invention features an expression vector for expression of a desired protein in a host from a first Streptomyces species. The vector includes the promoter DNA and the DNA encoding a signal sequence as described above and a structural gene coding for a desired protein. The DNA that encodes a signal sequence derives from DNA that occurs naturally in a second species of Streptomyces, and the vector is capable of expressing a preproduct in the Streptomyces host; the preproduct includes a signal sequence and the desired protein. The signal sequence permits secretion of a compound comprising the desired protein.

In a third aspect, the invention features an expression vector as described above except that the host and the source from which the DNA encoding a signal sequence derives are not necessarily different species of Streptomyces; and the structural gene is one that is not naturally transcribed and translated with the DNA encoding a signal sequence.

In a fourth aspect, the invention features a Streptomyces host cell that includes one of the above-described expression vectors.

In a fifth aspect, the invention features a method of making a desired protein by growing a Streptomyces host carrying one of the expression vectors, in a suitable medium and under suitable conditions, and recovering the compound comprising the protein from the medium.

In a sixth aspect, the invention features a method of evaluating a potential secretion vector or potential host gram positive bacterial strains using alkaline phosphatase. The secretion vector includes regulatory DNA as described above and DNA encoding a signal sequence. The method comprises providing a test vector comprising the secretion vector and DNA encoding for alkaline phosphatase positioned therein for transcription and translation of the DNA encoding a signal sequence and the alkaline phosphatase-coding DNA under control of the regulatory DNA. After transformation of gram positive host strain cells with the test vector, strain cells are cultured in a medium comprising an indicator responsive to extracellular alkaline phosphatase.

In preferred embodiments, the DNA encoding a signal sequence, the promoter sequence, or the ribosome-binding site, or all three, derive from the respective components associated with a Streptomyces endo H gene, most preferably that of *S. plicatus*. Alternatively, the promoter may derive from the promoter sequence from the neomycin resistance (aph) gene of *S. fradiae*. The cloning vector comprises a sequence enabling replication in Streptomyces, for example from pIJ702, and, in one embodiment, a sequence enabling replication in E. coli, for example from pBR322. The cloning vector also comprises a DNA sequence capable of conferring antibiotic resistance, for example to thiostrepton, on Streptomyces. Preferably, an antibiotic resistance gene effective in E. coli is also included, for example, one of the resistance genes of pBR322.

In preferred embodiments of the expression vectors, the structural gene is the endo H gene of S. plicatus or the alkaline phosphatase gene of E. coli.

In preferred embodiments of the cell and the method of production, the expression host may be one of the following species, without limitation: S. lividans, S. coelicolor, S. fradiae, S. griseofuscus, S. reticuli, S. rimosus, S. albus, S. parvulus, S. ambofaciens, S. aurofaciens, S. plicatus, S. espinosus, S. lincolnensis, S. erythresus, S. antibioticus, S. griseus, or S. glaucens. Most preferably, the host is S. lividans or S. coelicolor.

In preferred embodiments of the method of evaluating secretion vectors, after it is determined that alkaline phosphatase is secreted into the medium, a structural gene coding for a desired protein or peptide is inserted in a restriction endonuclease recognition site positioned in the secretion vector for transcription and translation of the DNA encoding a signal sequence and structural gene under control of the regulatory DNA. The preferred gram positive bacteria are members of the genus Streptomyces or the genus Bacillus (as defined in Bergey's manual, cited above).

The invention provides a versatile and generally useful cloning vector for Streptomyces that can be used to engineer an expression vector that includes any of a broad range of structural genes to be expressed with the DNA encoding a signal sequence and secreted into the medium surrounding the recombinant cells.

Streptomyces are particularly useful hosts for protein production for several reasons. In Streptomyces, antigenic lipopolysaccharide contaminants are not produced; a single membrane permeability barrier allows protein export into the culture medium; and secretion of a variety of proteins occurs in the regular course of growth. As with other gram positive bacteria, Streptomyces cells are capable of protein secretion because they lack a gram-negative outer membrane. Streptomyces generally do not produce toxic materials that must be separated from the desired product. Furthermore, the pharmaceutical industry has acquired extensive experience with large scale industrial growth and fermentation of Streptomyces strains, thus providing standard fermentation protocols. The life cycle of Streptomyces enables long time courses of high level production of desired proteins during the secondary stage of metabolism. High copy-number Streptomyces plasmids have been characterized, and genetically engineered derivatives are available for cloning purposes. The transcriptional and translational regulatory components of Streptomyces biosynthesis apparently do not limit expression of foreign genes.

Since the product is secreted, it is possible to obtain quantities that might be lethal if localized within the cell. Moreover, recovery of the product is simplified by the absence of intracellular contaminants and the avoidance of product purification therefrom. In addition, various cell-immobilization techniques are made more useful when the product is secreted into extracellular medium.

The method of evaluating potential secretion vectors and potential gram positive secretion hosts is a simple technique using an indicator that can be easily evaluated. Once promising candidates are isolated, a cloned gene coding for a desired protein can be inserted in the vector to enable expression of the protein in, and secretion of it from, the gram positive bacteria.

Other features and advantages of the invention will be apparent from the following description of the preferred embodiments thereof and from the claims.

DESCRIPTION OF THE PREFERRED EMBODIMENTS

We turn now to a description of the preferred embodiments of the invention, first briefly describing the drawings.

Figure 4:
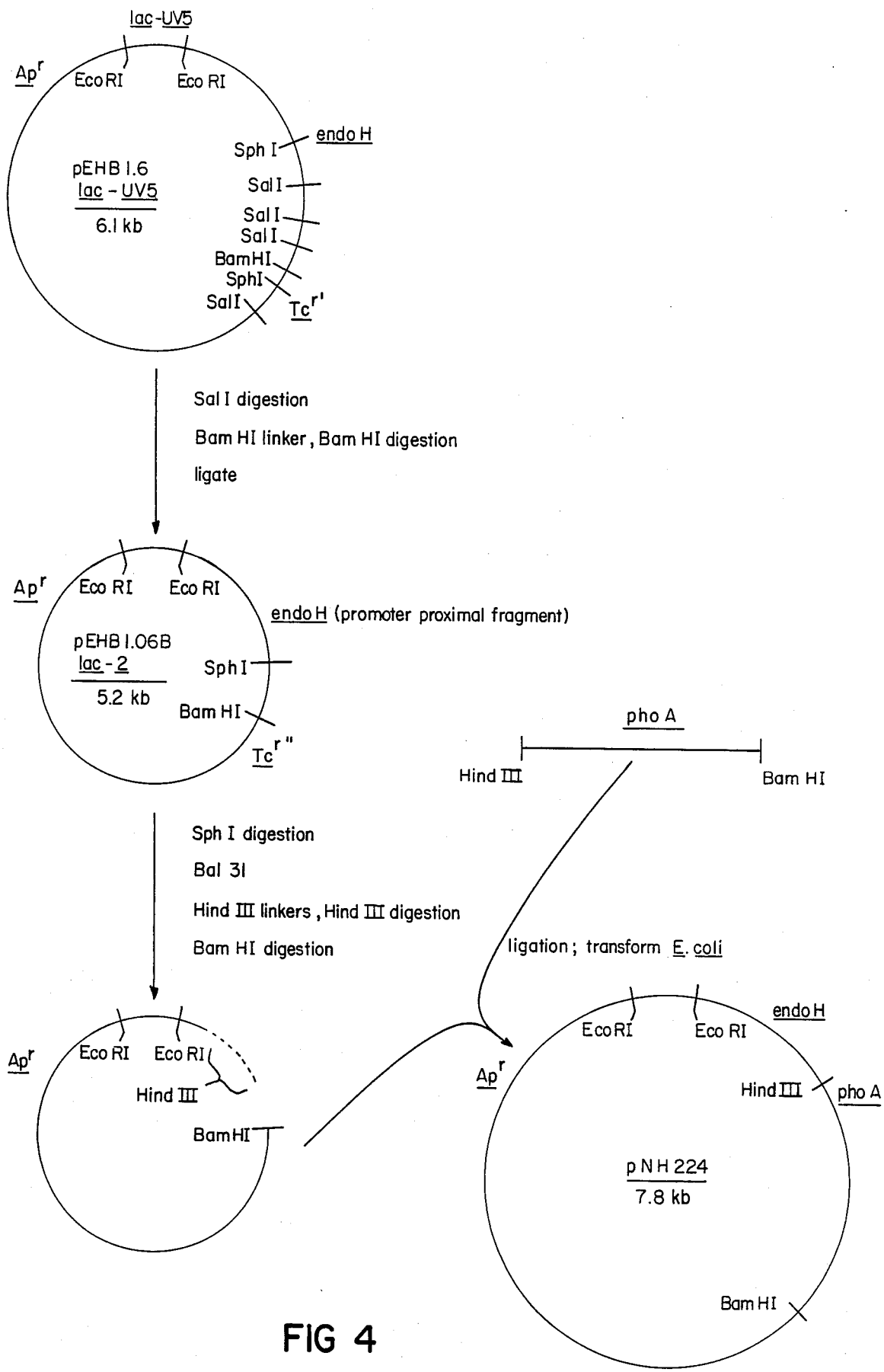
FIG. 4 is a flow diagram depicting construction of an expression vector.

The primary components of the expression and cloning vector are illustrated by the construction and structure of expression vectors pGH202 and pGH205, and by derivatives of pNH224, a vector shown in FIG. 4. pGH202 and pGH205, have been deposited with the American Type Culture Collection and they bear the following accession numbers, respectively: ATCC 39896 and ATCC 39895. Applicants' assignee, BioTechnica International, Inc. acknowledges its responsibility to replace these cultures should they die before the end of the term of a patent issued hereon, and its responsibility to notify the ATCC of the issuance of such a patent, at which time the deposits will be made available to the public. Until that time the deposits will be made available to the Commissioner of Patents under the terms of 37 CFR §1.14 and 35 USC §112.

The Vectors

Figure 3A:
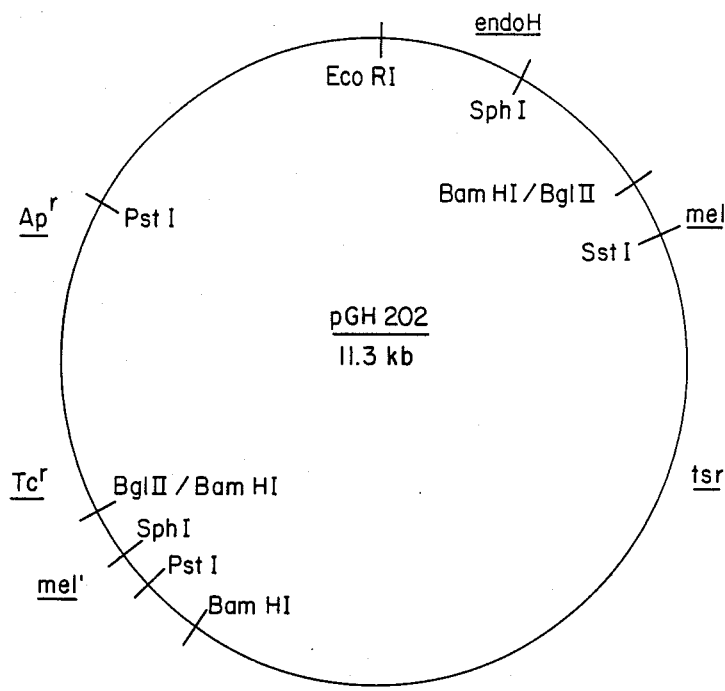
FIGS. 3A and 3B are restriction maps of pGH202 and pGH205, respectively.
Figure 3B:
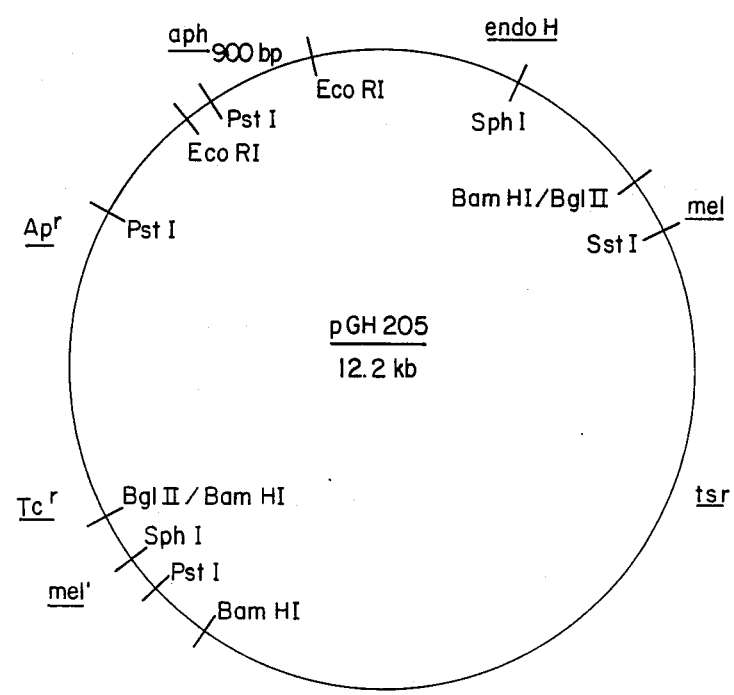

FIG. 3 shows maps of expression vectors pGH202 and pGH205 for expressing the secreted endo H. pGH202 and pGH205 contain the entire endo H gene from S. plicatus including a 600-bp region containing the transcriptional and translational regulatory controls of that gene. Of particular interest is the sequence of DNA that is about 120-bp long and that includes the DNA that encodes the signal sequence of that gene. The DNA sequence and resulting amino-acid sequence that functions as a signal sequence for endo H are included in the following sequences:

```
ATG TTC ACT CCG GTT CGC AGA AGG
  GTG CGG ACG GCT GCG CTC Met Phe Thr
  Pro Val Arg Arg Arg Val Arg Thr Ala Ala Leu

GCG CTC TCG GCC GCC GCG GCC CTC GTC
  CTC GGT TCC ACC GCC Ala Leu Ser Ala Ala
  Ala Ala Leu Val Leu Gly Ser Thr Ala

GCG AGC GGC GCG TCA GCG ACC CCC
  TCA CCC GCT CCG GCC CCG Ala Ser Gly
  Ala Ser Ala Thr Pro Ser Pro Ala Pro Ala Pro.
```

While it may be preferable to include in the expression vector the entire DNA sequence set out above, the secretion signaling ability does not require that entire sequence in every host. For example, primary cleavage may occur at one or more sites within one peptide residue of the 29th amino acid (Ala) of the above listed sequence, and the resulting 28-30 amino acids may be sufficient to enable secretion.

Other genetic components of pGH202 and pGH205 include:

1. pIJ702, including the promoter-proximal part of the mel gene from *S. antibioticus*, the tsr gene from *S. azureus*, the pIJ101 replicon, and the promoter-distal portion of the mel gene; and 2. the pBR322 fragment including the promoter distal portion of the gene for tetracycline-resistance, the pBR322 origin of replication, and the gene for ampicillin resistance.

pGH205 contains all of the genes known to be carried by pGH202, and, in addition, it includes the promoter of the aminoglycoside phosphotransferase (aph) gene coding for resistance to neomycin.

FIG. 4 shows construction of an expression vector for expressing *E. coli* alkaline phosphatase and containing the regulatory information discussed above regarding pGH202. Specifically, the vector includes the above-described DNA that encodes the *S. plicatus* endo H signal sequence and the structural gene for *E. coli* alkaline phosphatase.

pGH202 and pGH205 are bifunctional in that they replicate both in Streptomyces and in *E. coli* strains, and both vectors confer resistance to an antibiotic on each of those organisms, thus making them useful for engineering both in *E. coli* and Streptomyces. While such bifunctionality is preferred, the ability to replicate in *E. coli*, and an antibiotic resistance marker for *E. coli*, are not essential to the use of the vector as a Streptomyces secretion vector.

Construction of pGH202

Figure 1:
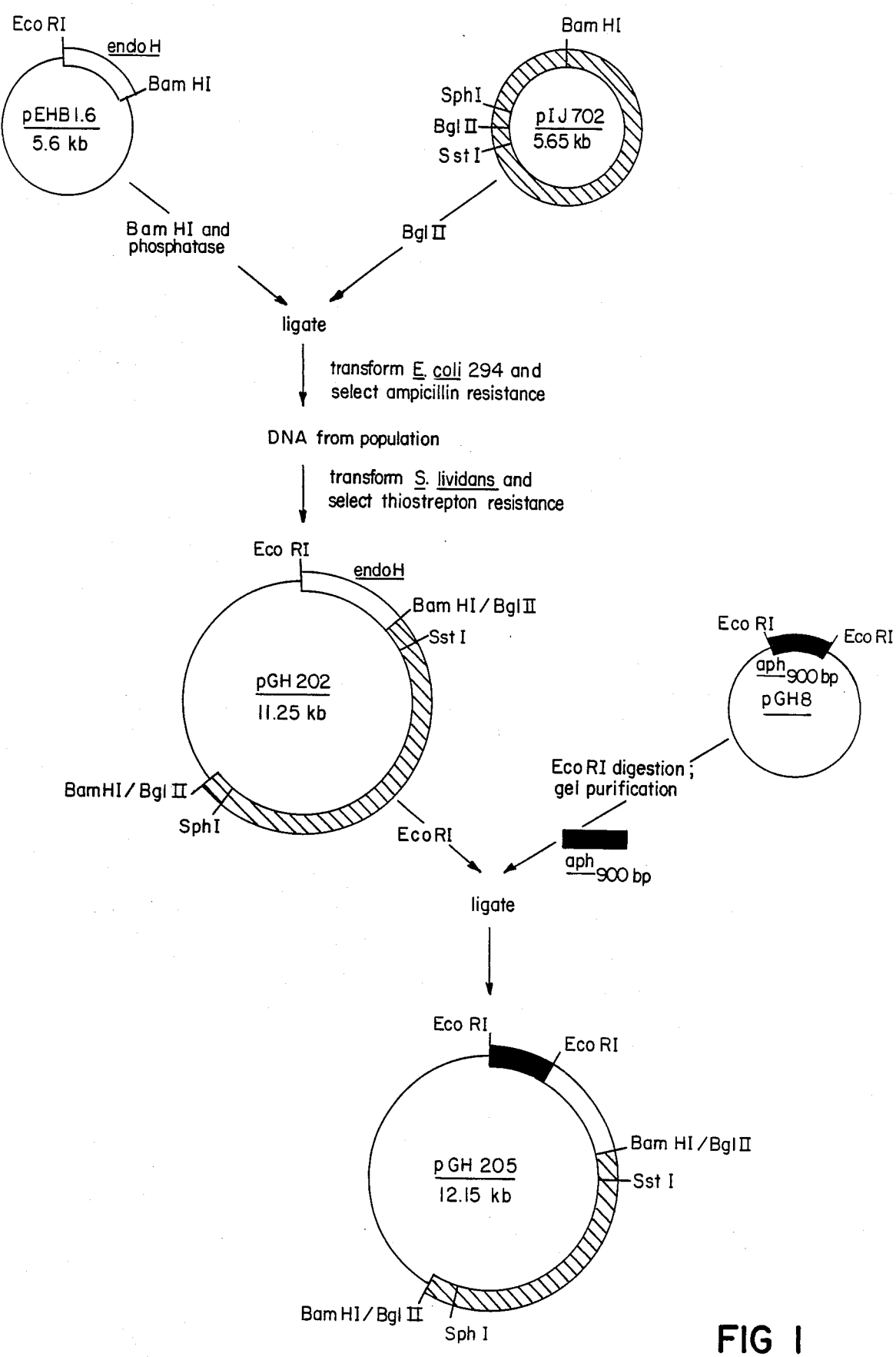
FIG. 1 is a flow diagram depicting construction of expression vectors pGH202 and pGH205.

Standard methods of recombinant DNA technology may be used to construct pGH202 as shown in FIG. 1. Following cleavage of plasmid pEHB1.6 from *S. plicatus* [described in Robbins et al. (1981) J. Biol. Chem. 256:10,640–10,644] with restriction enzyme BamHI, the plasmid is treated with alkaline phosphatase (calf intestinal) and ligated to plasmid pIJ702 DNA [disclosed in Katz et al. (1983) cited above and available from John Innes Institute, Norwich, England] that had been digested with BglII. These ligated plasmids are transformed into *E. coli* 294 (ATCC 33,625), and ampicillin-resistant derivatives are selected. Plasmid DNA isolated from a mixed population of *E. coli* transformants is then used to transform protoplasts of *S. lividans* to thiostrepton resistance, a genetic marker carried on the Streptomyces pIJ702 replicon. Transformants are isolated and plasmid DNA purified and characterized with respect to marker restriction sites.

Construction of pGH205

Figure 2:
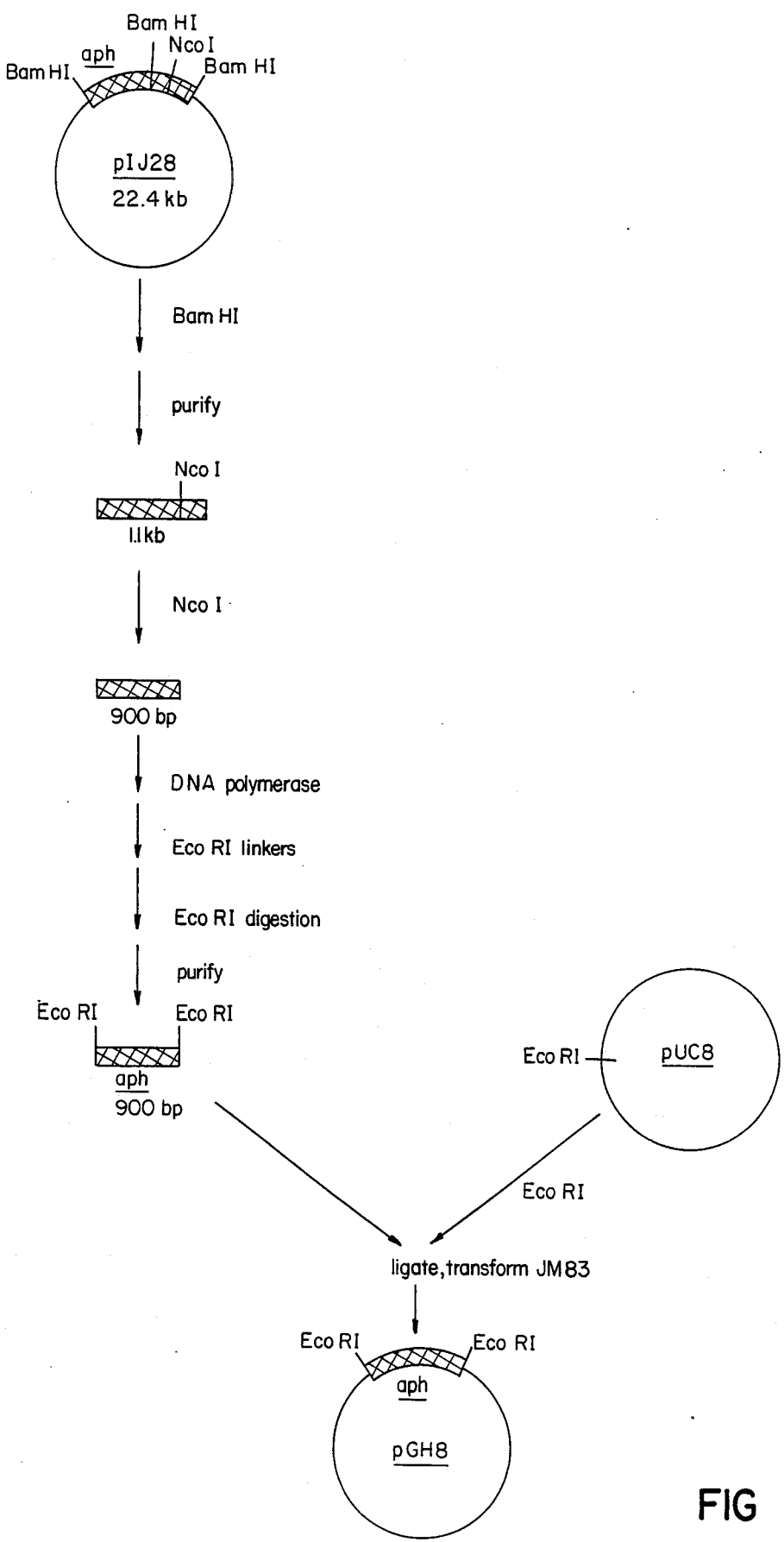
FIG. 2 is a flow diagram depicting construction of the vector pGH8.

As shown in FIG. 2, the promoter fragment of the gene for neomycin-resistance is isolated from the aph gene of *S. fradiae* carried on pIJ28 described by Hopwood et al. Ch. 4 *Genetic Engineering Principles and Methods*, pp. 119–145 Setlow et al. Eds. (Plenum Press, NY, 1982). Digestion of this plasmid with BamHI releases the aph gene as 1.1 kb promoter-proximal and 2.2 kb promoter-distal DNA fragments. The 1.1-kb fragment is purified by gel electrophoresis, digested with NcoI, and the resulting mixture of 900- and 200-bp pieces is subjected to treatment with DNA polymerase (Klenow fragment), ligation to EcoRI linkers, and digestion with EcoRI. The 900-bp promoter fragment with EcoRI ends is purified and ligated to EcoRI-digested plasmid pUC8, available from BRL. The reaction mixture is used to transform *E. coli* strain JM83, also available from BRL, and a strain bearing DNA with the aph fragment in the pUC8 backbone is selected from among JM83 cells using LB agar supplemented with ampicillin and X-gal (5'-bromo-4'-chloro-3'-indolyl-$\beta$-D-galactoside). The resulting plasmid, pGH8, is used as the source of DNA for further constructions involving the 900-bp aph promoter fragment, described below.

Digestion of pGH8 with EcoRI releases the aph promoter segment, which is mixed with pGH202 DNA that had been purified from an *E. coli* transformant and digested with EcoRI and treated with phosphatase (calf intestinal). This mixture is ligated and used to transform *E. coli*. Clones that are ampicillin-resistant and carry the 900-bp insert are identified and characterized for orientation of aph, and plasmid DNA from an appropriate clone is used to transform *S. lividans* protoplasts to thiostrepton resistance.

Other Expression Vectors

Streptomyces vectors for expressing and secreting other proteins may be constructed as illustrated in FIG. 4. The specific illustrative example of FIG. 4 includes the DNA that encodes the endo H signal sequence described above, linked to a cloned gene of interest such as the *E. coli* alkaline phosphatase gene (phoA). While alkaline phosphatase is a useful enzyme in its own right, it provides a particularly useful tool for screening potential secretion vectors for use in gram positive bacteria, particularly in Streptomyces, and for screening potential gram positive host strains. The potential secretion vector includes a promoter and other regulatory DNA that is functional in the bacteria of interest. The vector also includes a DNA that encodes a signal sequence whose function is to be evaluated with an alkaline phosphatase structural gene. Construction of such a vector is described below.

In general, a vector containing the DNA that encodes a signal sequence is cleaved at a site near the downstream end of the signal sequence. To optimize the distance between the DNA that encodes the signal sequence and the structural gene, the fragment terminus may be further digested and/or connected with a linker to permit insertion of the desired structural gene in position to be expressed in frame with the DNA that encodes the signal sequence. Cells containing such structures can be selected from the mixture with an appropriate assay for the desired compound, such as those described below for endo H and for alkaline phosphatase. A Streptomyces replicon should be added if it is not already present on the constructed vector.

The above general procedure is illustrated (FIG. 4) by construction of pNH224 derivatives.

First, pEHB1.6 lac-UV5 [Robbins et al. (1981) cited above] is treated to remove the SphI site from its pBR322 backbone leaving the SphI site downstream from the endo H signal sequence as the only SphI site on the vector (pEHB1.06B lac-2). This is accomplished by SalI digestion, insertion of a BamHI linker, BamHI digestion, and ligation.

The resulting plasmid (pEHB1.06B lac-2) is subjected to SphI digestion and to Ba131 digestion in order to obtain fragments with a terminus close to the end of the DNA sequence that encodes the signal sequence. Linkers (e.g. HindIII) are added to allow insertion of the structural gene phoA on segments having a HindIII proximal terminus and a BamHI distal terminus. The cloned phoA gene can be obtained from A. Wright, Department of Microbiology and Molecular Biology, Tufts University School of Medicine, Boston, Mass., or it can be obtained as described in Inouye et al., (1981) J. Bacteriol. 146:668-675.

By appropriate screening in E. coli, vector pNH224, which includes the phoA gene in proper reading frame and position, can be selected. Finally, pNH224 can be fused with DNA containing a Streptomyces replicon, such as pIJ702.

Expression of the Gene and Secretion of the Protein

The following description of the use of expression vectors pGH202, pGH205, and a derivative of pNH224 containing a Streptomyces replicon exemplify the featured expression strains and the featured method of producing a protein. Specifically, the production of endo H by, and use of alkaline phosphatase to monitor protein secretion from, S. lividans host cells is described.

Endo H is currently among the most expensive of commercially available enzymes. It is obtained from culture supernatants of a strain of Streptomyces plicatus (ATCC 27800) (previously classified as S. griseus) at yields of approximately 200 μg per liter, hence purification is cumbersome and yield very low. The unique enzyme specificity, cleavage of the glycosidic bond between two N-acetylglucosamine residues of high mannose oligosaccharides of cell-surface glycoproteins, makes endo H an important analytical tool for research on processing of cell surface components.

As indicated above, alkaline phosphatase serves as a convenient research tool to measure expression and secretion of proteins from Streptomyces and other gram positive bacteria. Convenient plate tests are available to monitor the secretion of alkaline phosphatase, such as assays using the dye X-P (5-bromo-3-chloro-indole phosphate) which turns blue upon cleavage by alkaline phosphatase, or assays using compounds such as para-nitrophenyl phosphate.

To produce a desired compound or to test for alkaline phosphatase secretion, S. lividans mycelia, carrying the appropriate plasmid constructed as described above, is grown in an appropriate medium at 30° C. with aeration. For example, the broth may be YEME broth having the following constituents per liter: Difco yeast extract, 3 g; Difco peptone, 5 g; Oxoid malt extract, 3 g; glucose, 10 g; sucrose 340 g; MgCl$_2$ added to 5mM after autoclaving. Samples of culture taken at various time points are centrifuged, and supernatant fractions assayed for the product. For example, endo H may be assayed as described by Robbins et al. (1981), cited above; and alkaline phosphatase may be assayed by the production of yellow color as described by Brickman and Beckwith (1975) J. Mol. Biol. 96:1-10.

The protein of interest is translated and secreted in substantial quantities, permitting efficient recovery and purification from the extracellular growth medium. Maximum secretion is obtained after 7-10 days.

Other Embodiments

Other embodiments are within the following claims. For example, and not by way of limitation, structural genes for other proteins such as calf rennin, insulin, growth hormone, interleukins, erythropoietin, tissue plasminogen activator, or hoof-and-mouth disease antigens may be inserted in place of the E. coli alkaline phosphatase gene described above. Various fermentation techniques that are known for Streptomyces fermentation processes may be used—for example, various cell immobilization techniques may be used.

We claim:

1. A DNA vector for producing a desired protein in a Streptomyces host, said vector comprising the following components:
   (a) a DNA sequence coding for a signal sequence, wherein said sequence is identical to the DNA signal sequence of a Streptomyces endoH gene, or an engineered or chemically synthesized variant thereof;
   (b) a structural gene that codes for the desired protein, wherein said gene comprises DNA that is not naturally transcribed and translated with said DNA coding for a signal sequence wherein said gene is operably linked to said DNA signal sequence; and
   (c) regulatory DNA that includes a promoter sequence effective to start transcription in said host Streptomyces, said promoter being positioned and oriented in said vector to initiate transcription toward the signal sequence-encoding DNA and the structural gene.

2. A DNA vector for producing a desired protein in a Streptomyces host, said vector comprising the following components:
   (a) a DNA sequence coding for a signal sequence, wherein said sequence is identical to the DNA signal sequence of a Streptomyces endoH gene, or an engineered or chemically synthesized variant thereof;
   (b) an engineered restriction site positioned to receive DNA that codes for a protein to be secreted and that is not naturally translated and transcribed with said DNA coding for a signal sequence wherein said restriction site is operably linked to said DNA signal sequence; and
   (c) regulator DNA that includes a promoter sequence effective to start tanscription in said host Streptomyces, wherein said promoter is positioned and oriented in said vector to initiate transcription toward the signal sequence-encoding DNA and the structural gene.

3. The vector of claim 1 or claim 2 wherein said Streptomyces endoH gene is from the species S. plicatus.

4. The vector of claim 1 or claim 2 wherein said promoter sequence is identical to, an engineered variant of, or a chemically synthesized variant of, a promoter sequence that occurs in a Streptomyces endoH gene.

5. The vector of claim 4 where said promoter sequence is identical to, an engineered variant of, or a chemically synthesized variant of, the S. plicatus endoH promoter.

6. The vector of claim 1 or claim 2 where said promoter sequence is identical to, an engineered variant of, or a chemically synthesized variant of, the promoter sequence of the aph gene of S. fradiae.

7. The vector of claim 2 where said restriction endonuclease recognition site in SphI or HindIII.

8. The vector of claim 1 or claim 2 where said signal sequence comprises the sequence:

Met Phe Thr Pro Val Arg Arg Arg Val Arg Thr Ala
Ala Leu Ala Leu Ser Ala Ala Ala Ala Leu Val
Leu Gly Ser Thr Ala Ala Ser.

9. The vector of claim 3 wherein said *S. plicatus* DNA encoding said signal sequence comprises:

```
ATG TTC ACT CCG GTT CGC AGA AGG
   GTG CGG ACG GCT GCG CTC GCG CTC
   TCG GCC GCC GCG GCC CTC GTC CTC
   GGT TCC ACC GCC GCG AGC.
```

10. The vector of claim 1 or 2 where said DNA sequence comprises DNA coding for the sequence:

```
Met Phe Thr Pro Val Arg Arg Arg Val Arg Thr Ala
   Ala Leu Ala Leu Ser Ala Ala Ala Ala Leu Val
   Leu Gly Ser Thr Ala Ala Ser Gly Ala Ser Ala Thr
   Pro Ser Pro Ala Pro Ala Pro.
```

11. The vector of claim 1 or 2 where said DNA sequence comprises the sequence:

```
ATG TTC ACT CCG GTT CGC AGA AGG
   GTG CGG ACG GCT GCG CTC GCG CTC
   TCG GCC GCC GCG GCC CTC GTC CTC
   GGT TCC ACC GCC GCG AGC GGC GCG
   TCA GCG ACC CCC TCA CCC GCT CCG
   GCC CCG.
```

12. The vector of claim 1 or claim 2 wherein said vector comprises at least one replication sequence engineered from the Streptomyces plasmid pIJ702.

13. The vector of claim 1 or claim 2 wherein said vector comprises at least one sequence enabling replication in *E. coli*.

14. The vector of claim 1 or claim 2 which also comprises a DNA sequence capable of conferring antibiotic resistance on Streptomyces.

15. The vector of claim 14 where said antibiotic is thiostrepton.

16. The vector of claim 13 which also includes DNA sequences capable of conferring antibiotic resistance on *E. coli* cells.

17. The vector of claim 16 where said antibiotic-resistance and replication-enabling sequences are segments from pBR322.

18. A host Streptomyces bacterial cell from a species other than *S. plicatus*, said host cell comprising an expression vector comprising:

(a) a DNA sequence coding for a signal sequence, said DNA sequence being identical to a DNA sequence that occurs in the endoH gene of *S. plicatus* or an engineered or chemical derivative thereof;

(b) a structural gene that codes for a desired protein wherein said gene is operably linked to said DNA signal sequence; and (c) regulatory DNA that includes a promoter sequence effective to start transcription in said host Streptomyces, said promoter being positioned and oriented in said vector to initiate transcription toward the signal sequence-encoding DNA and the structural gene.

19. The cell of claim 18 where said structural gene is identical to, an engineered derivative of, or a chemical derivative of, a gene coding for endoH.

20. The cell of claim 18 comprising a plasmid selected from the group consisting of pGH202, as in strain number ATCC 39896, pGH205, as in strain number ATCC 39895 and functionally equivalent engineered derivatives thereof.

21. A Streptomyces cell comprising the vector of claim 1.

22. A cell according to claim 18 or claim 21 that is a member of the species *S. lividans* or *S. coelicolor*.

23. An expression vector, wherein said vector is pGH202, as in strain number ATCC 39896 or pGH205, as in strain number ATCC 39895.

24. A method of producing a desired protein comprising culturing cells of a strain of Streptomyces according to claim 18 or claim 21 in a culture medium and recovering the protein product of said strcutural gene from the medium.

25. The cell of claim 18 wherein said promoter is a Streptomyces promoter selected from the group consisting of the promoter naturally associated with the endoH gene of *S. plicatus* and the promoter naturally associated with the aph gene of *S. fradiae*.

26. A cell according to claim 21 wherein said cell is a species selected from the group consisting of *S. lividans, S. coelicolor, S. fradiae, S. griseofuscus, S. reticuli, S. rimosus, S. albus, S. parvulus, S. ambofaciens, S. aureofaciens, S. plicatus, S. espinosus, S. lincolnensis, S. erythreus, S. antibioticus, S. griseus,* and *S. glaucescens*.

* * * * *